(12) United States Patent
He et al.

(10) Patent No.: US 6,423,790 B1
(45) Date of Patent: Jul. 23, 2002

(54) BIODEGRADABLE POLY(PROPYLENE FUMARATE) NETWORKS CROSS LINKED WITH POLY(PROPYLENE FUMARATE)-DIACRYLATE MACROMERS

(75) Inventors: Shulin He, Houston, TX (US); Michael J. Yaszemski, Rochester, MN (US); Antonios G. Mikos, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 09/549,485

(22) Filed: Apr. 14, 2000

Related U.S. Application Data (60) Provisional application No. 60/129,577, filed on Apr. 16, 1999, provisional application No. 60/146,991, filed on Aug. 3, 1999, provisional application No. 60/167,328, filed on Nov. 24, 1999, and provisional application No. 60/167,388, filed on Nov. 24, 1999.

(51) Int. Cl.[7] .................... C08L 67/06; C08L 67/07; A61K 6/00

(52) U.S. Cl. ........................................ 525/445; 523/116
(58) Field of Search ........................... 525/445; 523/116

(56) References Cited

U.S. PATENT DOCUMENTS

| 4,722,948 | A | * | 2/1988 | Sanderson ................... 525/445 |
| 4,888,413 | A | * | 12/1989 | Domb ..................... 424/78.17 |
| 5,286,763 | A | | 2/1994 | Gerhart et al. ............ 514/772.4 |
| 5,527,864 | A | | 6/1996 | Suggs et al. ................. 525/444 |
| 5,733,951 | A | * | 3/1998 | Yaszemski et al. ......... 523/116 |
| 6,124,373 | A | * | 9/2000 | Peter et al. ................. 523/116 |

OTHER PUBLICATIONS

Domb et al., Biomaterials 17 (1996) 411–417).*

* cited by examiner

Primary Examiner—D. R. Wilson
(74) Attorney, Agent, or Firm—Conley, Rose & Tayon, P.C.

(57) ABSTRACT

A network consisting essentially of poly(propylene fumarate) cross linked with diacrylate and a method for making same.

12 Claims, 7 Drawing Sheets

BIODEGRADABLE POLY(PROPYLENE FUMARATE) NETWORKS CROSS LINKED WITH POLY(PROPYLENE FUMARATE)-DIACRYLATE MACROMERS

RELATED CASES

The present case claims the benefit of U.S. provisional applications Serial No. 60/129,577, filed Apr. 16, 1999, and entitled "Development of Biodegradable Bone Cement Based on Poly(Propylene Fumarate) and a Macromer," Serial No. 60/146,991, filed Aug. 3, 1999, and entitled "Synthesis of Poly (Propylene Fumarate) by Acylation of Propylene Glycol in the Presence of a Proton Scavenger," Serial No. 60/167,328, filed Nov. 24, 1999, and entitled "Preparation of an Injectable, in situ Polymerizable and Biodegradable Biomaterial Based On Poly(Propylene Fumarate) and Biodegradable Crosslinking Reagents," and Serial No. 60/167,388, filed Nov. 24, 1999, and entitled "Injectable Biodegradable Polymer Composites Based on Poly(Propylene Fumarate) Crosslinked with Poly(Ethylene Glycol) Dimethacrylate and $\beta$-Tricalcium Phosphate," all of which are incorporated herein by reference.

STATEMENT REGARDING FEDERALLY SPONSORED RESEARCH OR DEVELOPMENT

This work was funded by the National Institutes of Health R01-AR44381 and R01-DE13031.

TECHNICAL FIELD OF THE INVENTION

This invention relates to a compound for replacing or reconstructing rigid or semi-rigid living tissue. More particularly, the present invention relates to a compound comprising biodegradable poly(propylene fumarate) networks, which may be crosslinked with diacrylate macromers, and a method for making same.

BACKGROUND OF THE INVENTION

In the field of tissue engineering, degradable biomaterials usually serve as a scaffold to provide mechanical support and a matrix for the ingrowth of new tissue. As new tissue forms on the scaffold, the biomaterial degrades until it is entirely dissolved. The degradation products are eliminated through the body's natural pathways, such as metabolic processes.

One example of the use of such biomaterials is as a temporary bone replacement. It is often desired to replace or reconstruct all or a portion of a living bone, such as when a bone has been broken or has been resected as a result of a bone tumor. In these instances, the missing bone can be replaced with a mechanical device, such as a pin, plate or the like, or it can be replaced with an implant that is designed to more closely resemble the original bone itself. Often these implants comprise biodegradable polymeric compounds or parts made from such compounds. It is contemplated that bone tissue will grow back into the pores of the implant and will gradually replace the entire implant as the implant itself is gradually degraded in the in vivo environment. For obvious reasons then, such implants should be biocompatible and non-toxic.

Similarly, the use of biodegradable polymers for temporary surgical and pharmacological applications such as drug delivery has been explored recently. Aliphatic polyesters and anhydrides are the polymer families that have been recognized as the most attractive and promising.

Poly(propylene fumarate) (PPF) is one such polymer. Poly(propylene fumarate) (hereinafter "PPF") is an unsaturated linear polyester that degrades in the presence of water into propylene glycol and fumaric acid, degradation products that are easily cleared from the human body by normal metabolic processes. Because the fumarate double bonds in PPF are reactive and crosslink at low temperatures, it has potential to be an effective in situ polymerizable biomaterial. The crosslinking reaction can be carried out at a defect site using a benzoyl peroxide initiator, which is particularly interesting for orthopaedic applications in filling irregularly shaped defects with minimal surgical intervention. Several PPF-based formulation methods have been evaluated by varying such parameters as the molecular weight of PPF and the choice of crosslinking reagents. For example, U.S. Pat. No. 5,733,951 discloses a composite mixture incorporating P(PF), a crosslinking monomer (N-vinyl pyrrolidone), a porogen (sodium chloride), and a particulate phase ($\beta$-tricalcium phosphate) that can be injected or inserted into skeletal defects of irregular shape or size.

As in the '951 patent, much of the previous work involving PPF used n-vinyl pyrrolidone (NVP) as a crosslinking reagent. The crosslinking agent bonds at its ends to separate, larger propylene fumarate molecules, serving as a link or bridge between them. While these compounds exhibit promising characteristics, it is believed preferable to avoid the presence of any unreacted NVP after in situ polymerization. Also, the poly(vinyl pyrrolidone) (PVP) links in the crosslinked PPF networks are non-degradable.

It is possible to use poly(ethylene glycol)-dimethacrylate (PEG-DMA) as a crosslinking reagent to form PPF polymer networks. PPF/PEG-DMA composites appear to posses ideal initial mechanical properties. These desired properties decrease in the wet state, however, due to the hydrophilicity of PEG. Hence, in order to retain the favorable mechanical properties, it is desirable to avoid high degrees of water absorption.

Another important factor in the success of biomaterials development is the nature of the degradation products. Although degradation of PPF-based polymer composites has been studied to assess the mass loss and the change of mechanical properties, the degradation products have not been characterized.

Hence, it is desired to provide biodegradable PPF-based polymer networks that do not require the use of NVP, are biodegradable, have desired mechanical properties in both dry and wet states, and that degrade into non-toxic degradation products.

SUMMARY OF THE INVENTION

The present invention includes the use of PPF-diacrylate (PPF-DA) as a crosslinking reagent in the polymerization of PPF. As discussed below, the effects of double bond ratio of PPF/PPF-DA and molecular weight of PPF-DA on the mechanical properties of the crosslinked polymer networks as well as on their equilibrium water content have been evaluated. It has been discovered that the degradation reaction of the PPF/PPF-DA polymer networks yields degradation products that are non-toxic and readily metabolized. The present invention includes methods for make novel compounds, including polymeric networks consisting essentially of cross linked PPF, poly(propylene fumarate) networks cross linked with diacrylate, cross linkable compositions comprising PPF-DA, and poly(propylene fumarate) networks crosslinked with diacrylate macromers. The inventive methods include making a polymer network by forming propylene fumarate (PF) by the reaction of fumaryl chloride with propylene glycol, transesterifying the PF to give PPF, synthesizing PPF-DA by reacting the PPF with an acrylation reagent; and cross-linking the PPF-DA, as well as the intermediate steps of this process.

As used herein, the term "network" refers to polymeric molecules that have been cross linked so as to effectively form a continuous molecule. The term "gel" is sometimes used to refer to the same type of cross linked systems.

BRIEF DESCRIPTION OF THE DRAWINGS

For a better understanding of the present invention, reference will be made to the attached Figures, wherein.

DETAILED DESCRIPTION OF A PREFERRED EMBODIMENT

According to a preferred embodiment of the present invention, new biodegradable poly(propylene fumarate)-based polymer networks are prepared by radical polymerization using poly(propylene fumarate) (PPF) and poly(propylene fumarate)-diacrylate (PPF-DA) macromers. The resulting PPF-DAs have negligible water content, and good compressive strength and compressive modulus. To illustrate and confirm the invention, two PPF-DAs were synthesized, incorporating one (m=1) and three (m=3) fumarate units respectively, and were employed in the synthesis of the polymer networks.

It has been discovered that the cross linked polymers of the present invention can be synthesized using a novel two-step technique. In the first step, di(2-hydroxylpropyl) fumarate is obtained by the reaction of fumaryl chloride with propylene glycol. Transesterification of di-(2-hydroxylpropyl) fumarate without any added catalyst produces PPF. The molecular weight of the PPF can be controlled by varying the transesterification time. In the second step PPF-DA is synthesized by reaction of PPF with acryloyl chloride.

Synthesis of PPF

Figure 1:
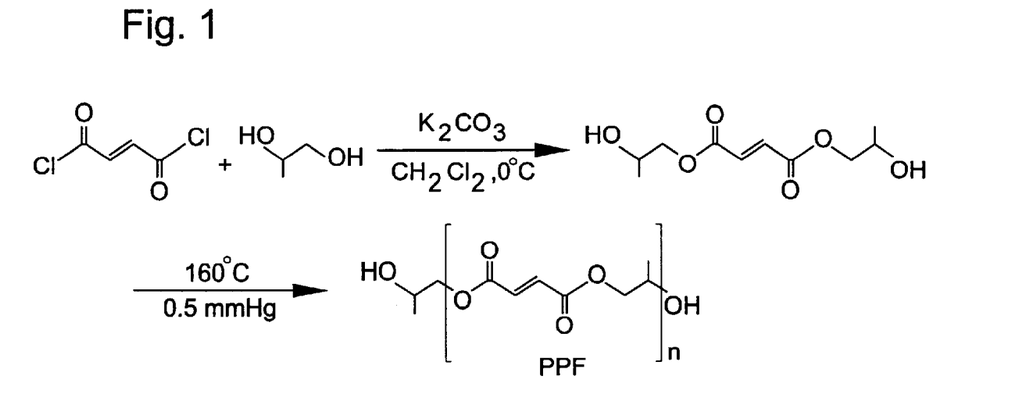
FIG. 1 is a schematic chemical diagram illustrating the synthesis of poly(propylene fumarate)

PPF is preferably prepared by the method generally described in co-pending application Ser. No. PCT/US99/07912, filed Apr. 9, 1999, and entitled "Synthesis of Poly (Proplyene Fumarate) by Acylation of Propylene Glycol in the Presence of a Proton Scavenger," which is incorporated herein by reference. The reaction is believed to proceed according to the mechanism shown in FIG. 1. In one embodiment, fumaryl chloride is added to a solution of propylene glycol in methylene chloride at 0° C. under nitrogen in the presence of $K_2CO_3$. After addition of the fumaryl chloride, the reaction mixture is stirred for an additional 2 h at 0° C., followed by the addition of water to dissolve the inorganic salt. The organic layer is separated and dried with $Na_2SO_4$. After filtration and evaporation of the solvent, the produced di-(2-hydroxylpropyl) fumarate underwent a transesterification reaction to produce PPF at a temperature of 160° C. and a pressure of 0.5 mm Hg. The resulting PPF can be purified through solution precipitation in chloroform and petroleum ether.

Figure 2:
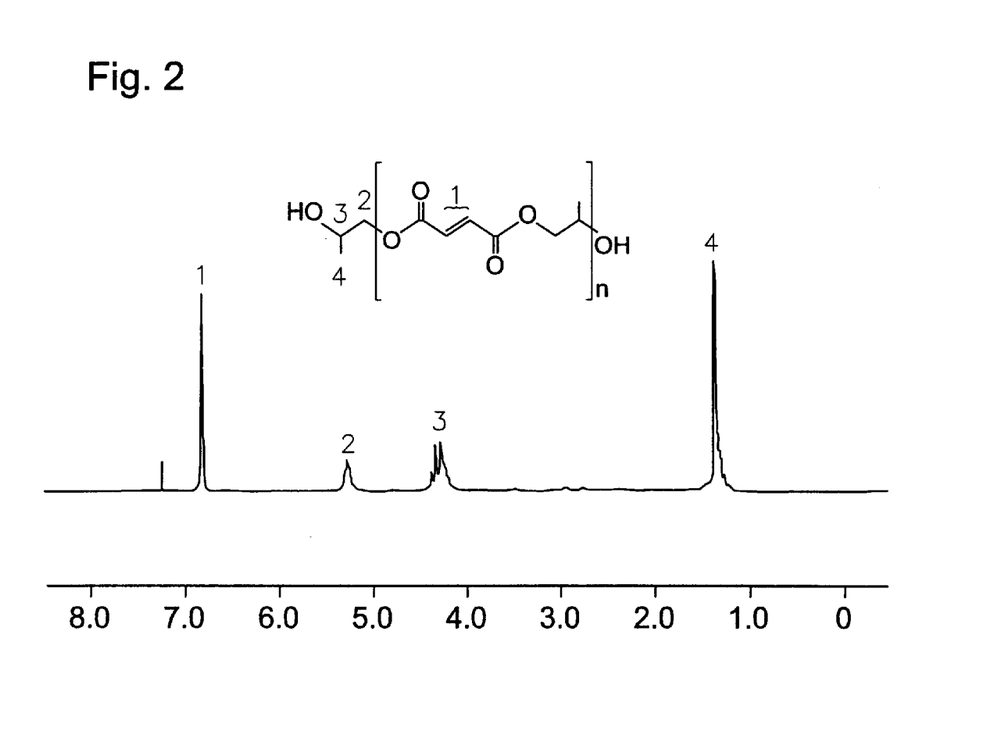
FIG. 2 is a $^1$H NMR spectrum for a PPF.
Figure 3:
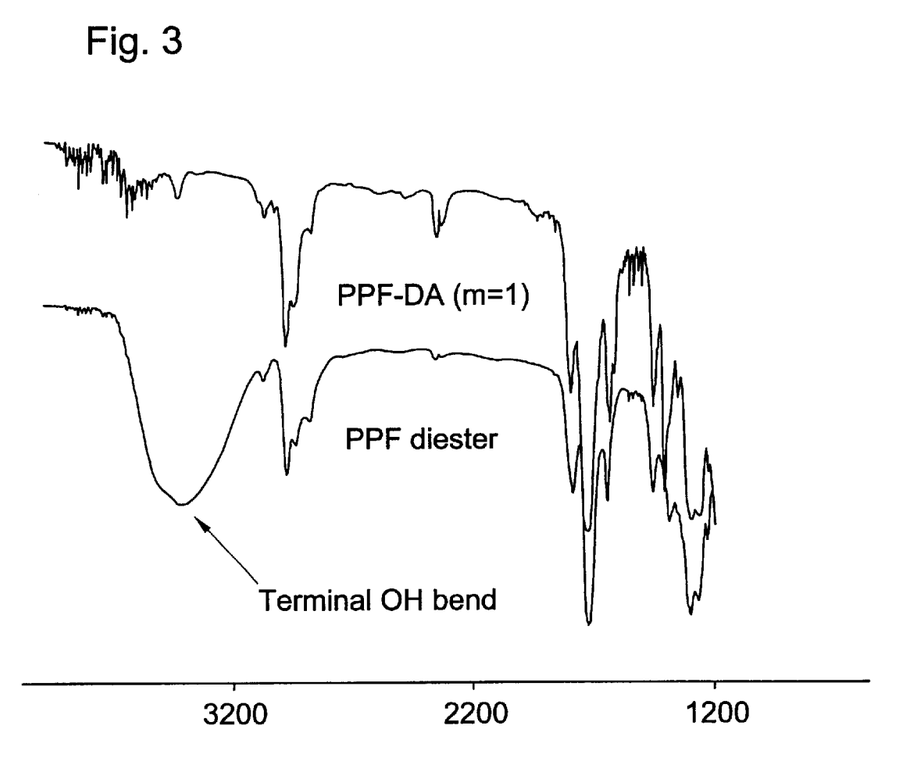
FIG. 3 is a plot of FTIR spectra for a PPF oligomer and an PPF-DA (m=1)

The structure of a PPF prepared according to this technique was analyzed by NMR and FTIR. NMR spectra were acquired in CDC13 on a Bruker AC-250 spectrometer. FTIR spectra were obtained on a Nicolet 550 spectrometer (Madison, Wis.) using neat samples. FIG. 2 is the $^1$H-NMR (250 MHz, CDC13) spectrum for the purified PPF, showing peaks at: 1.28 (m, 3H, $CH_3$), 4.26 (m, 2H, $CH_2$), 5.27 (m, 1H, CH), 6.84 (bs, 2H, —CH═CH—), and FIG. 3 shows FTIR spectra of (a) PPF oligomer and (b) PPF-DA (m=1) (discussed below);

Synthesis of PPF-DA

Figure 4:
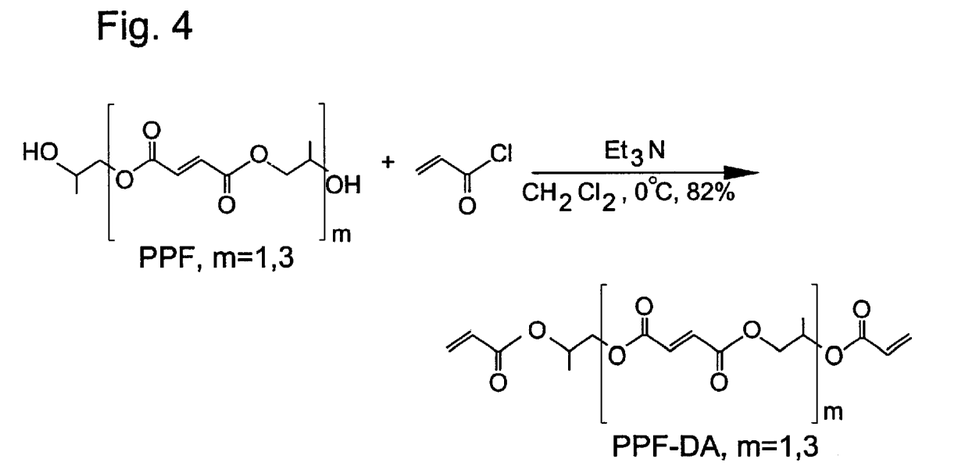
FIG. 4 is a schematic chemical diagram illustrating the synthesis of PPF-diacrylate (m=1,3)

FIG. 4 shows a believed mechanism for the synthesis reactions of PPF-diacrylate, using PPF as a starting point. A preferred procedure for synthesis of PPF-DA (m=1) in accordance with the present invention is as follows. Di-(2-hydroxylpropyl) fumarate obtained from the reaction of fumaryl chloride with propylene glycol described above is dissolved in dry $CH_2Cl_2$. To this solution at 0° C. is added triethylamine. After mixing thoroughly, acryloyl chloride is added slowly, causing formation of a white precipitate. The reaction mixture is preferably stirred overnight at room temperature. The white precipitate is filtered off and the $CH_2Cl_2$ solvent is removed by any suitable technique, such as rotary evaporation. Ethyl acetate is added to the residue and the ethyl acetate solution is washed with aqueous NaOH (5%), water and brine. After drying over $Na_2SO_4$, the mixture is filtered and the solvent evaporated, yielding PPF-DA. Alternatively, appropriate proton scavengers such as potassium carbonate can be used to replace triethylamine in this synthetic method.

Figure 5:
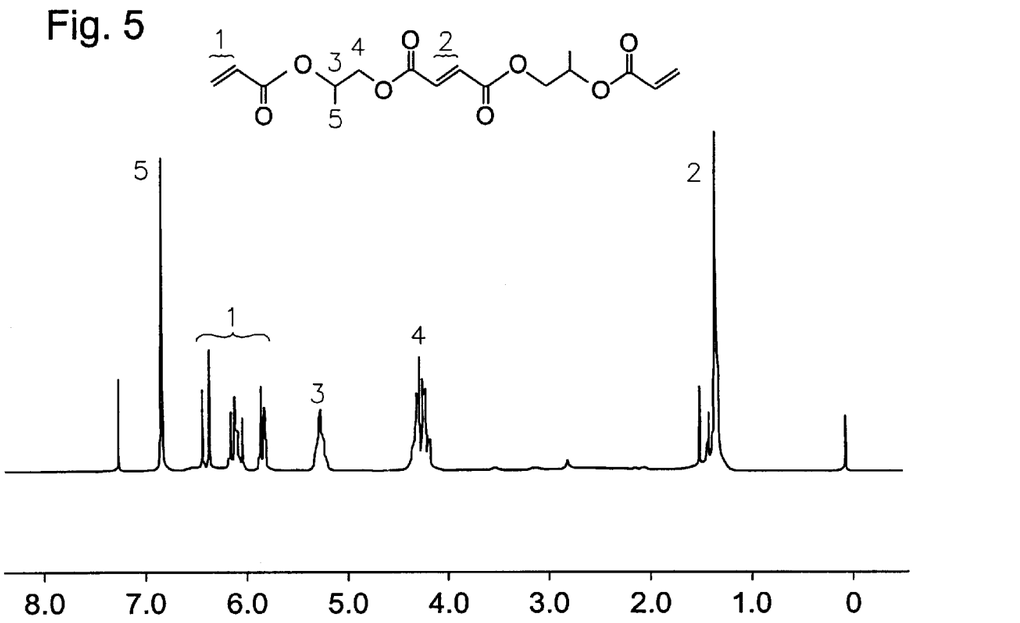
FIG. 5 is a $^1$H NMR spectrum of PPF-DA (m=1)

As with the PPF, the structure of a PPF-DA prepared according to this technique was analyzed by NMR and FTIR. FIG. 5 is the $^1$H-NMR (250 MHz, $CDCl_3$) spectrum for the PPF-DA, showing peaks at 1.32 (m, 3H, $CH_3$), 4.26 (m, 2H, $CH_2$), 5.24 (m, 1H, CH), 5.85 (m, 1H,—CH═$CH_2$), 6.05 (m, 1H, —CH═$CH_2$), 6.37 (dd, 1H, —CH═$CH_2$), 6.84 (bs, —CH═CH—). FIG. 3 shows the FTIR spectrum for PPF-DA (m=1). For synthesis of PPF-DA (m=3), PPF (m=3) obtained by the transesterification reaction can be used instead of di-(2-hydroxylpropyl) fumarate. Similarly, for synthesis of PPF-DA (m=x), PPF (m=x) is used as the starting reagent.

The integration ratio of the vinyl protons to the methyl protons is 2/3.6, which is close to the 2/3.4 calculated based on the number average molecular weight of PPF. This agreement indicated no loss of polymer unsaturation during the two step synthesis.

Preparation of PPF/PPF-DA Networks

Figure 6:
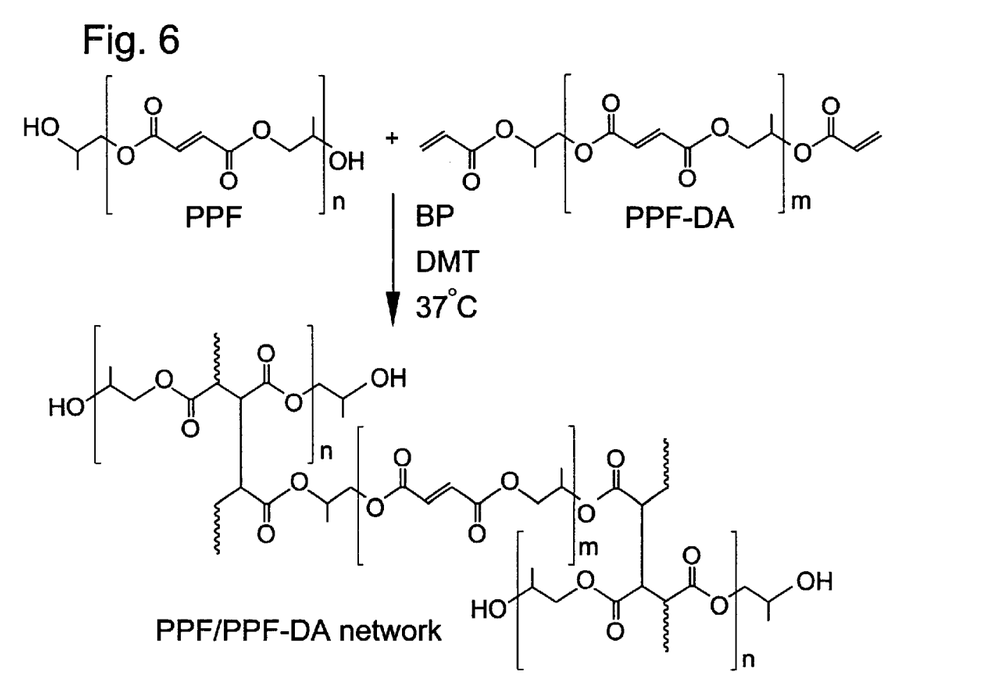
FIG. 6 is a schematic chemical diagram illustrating the synthesis of PPF/PPF-DA polymer networks.

FIG. 6 shows a believed mechanism for the synthesis of PPF/PPF-DA polymer networks, using PPF-DA prepared as described above as a starting point. A preferred procedure for their preparation is as follows. PPF is mixed with PPF-DA at room temperature such that the double bond ratio of PPF/PPF-DA is 1. Benzoyl peroxide (BP) is dissolved in $CH_2Cl_2$ and the solution is added to the PPF/PPF-DA mixture. After thorough mixing, N,N-dimethyl-p-toluidine (DMT) is added with rapid stirring, after which the mixture can be molded as a cylinder, film, or other shape. The networking step, and also the preceding steps, can be carried out in the presence of a catalyst such as $K_2CO_3$, if desired. If a catalyst is used, it can be easily removed from the final product with washing.

The resulting polymer networks are relatively highly hydrophobic, which enables them to maintain their mechanical properties in a wet environment, such as an in vivo environment. They are also osteoconductive, which makes them particularly suitable for use as bone replacement compounds. It has been found that, in contrast to previously known systems, the chain length of the present compounds can be controlled.

EXAMPLE

Samples comprising PPF/PPF-DA networks were made according to the technique described above. Variations on this formulation were made as needed to enable the interdependence of different features to be determined.

Materials

Propylene glycol, fumaryl chloride, benzoyl peroxide (BP), N,N-dimethyl-p-toluidine (DMT), and acryloyl chloride were purchased from commercial sources. Solvents such as methylene chloride, ethyl acetate and petroleum ether were also purchased from commercial sources and used as received. Fumaryl chloride was purified by distillation at 1 atm under nitrogen.

PPF was synthesized by the preferred two-step reaction process described previously. Specifically, fumaryl chloride was added dropwise to a solution of propylene glycol in methylene chloride at 0° C. under nitrogen in the presence of $K_2CO_3$. After addition of fumaryl chloride, the reaction mixture was stirred for an additional 2 h at 0° C. and then water was added to dissolve the inorganic salt. The organic layer was separated and dried with $Na_2SO_4$. After filtration and evaporation of the solvent, the formed di-(2-hydroxylpropyl) fumarate underwent transesterification reaction to produce PPF at a temperature of 160° C. and a pressure of 0.5 mm Hg. PPF was purified through solution precipitation in chloroform and petroleum ether. $^1$H-NMR (250 MHz, $CDCl_3$): $\delta$1.28 (m, 3H, $CH_3$), 4.26 (m, 2H, $CH_2$), 5.27 (m, 1H, CH), 6.84 (bs, 2H, —CH═CH—). PPF having a number average molecular weight of 1700 Da (n=11) and polydispersity index of 1.98 was obtained after 15 h transesterification.

Di-(2-hydroxylpropyl) fumarate was obtained from the reaction of fumaryl chloride with propylene glycol as described above. To a solution of di-(2-hydroxylpropyl) fumarate (23.2 g, 0.1 mol) in dry $CH_2Cl_2$ (200 mL) at 0° C. was added triethylamine (30.3 g, 0.3 mol). After stirring for 10 min, acryloyl chloride (26 g, 0.3 mol) was added dropwise during approximately 2 h, causing formation of a white precipitate. The reaction mixture was stirred overnight at room temperature. The white precipitate was filtered off and the $CH_2Cl_2$ solvent was rotary evaporated. Ethyl acetate (250 mL) was added to the residue and the ethyl acetate solution was washed with aq. NaOH (5%), water and brine. After drying over $Na_2SO_4$, filtration of the mixture and solvent evaporation, PPF-DA was obtained (28.5 g, 83%). For synthesis of PPF-DA (m=3), PPF (m=3) obtained by the transesterification reaction was used instead of di-(2-hydroxylpropyl) fumarate.

For the synthesis of PPF/PPF-DA polymer networks, 1 g PPF was mixed with 1.13 g PPF-DA (the double bond ratio of PPF/PPF-DA is 1) at room temperature. 6.5 mg BP were dissolved in 0.1 mL of $CH_2Cl_2$ and the solution was added to the PPF/PPF-DA mixture. After thorough mixing on Vortexer, 4 µL DMT were added with rapid stirring, then, the mixture was molded as a cylinder or a film. For mechanical testing, the mixture was placed into cylindrical vials of 6 mm diameter suspended in a 37° C. water bath. After 2 h, the cylinders were removed from the vials and cut into 12 mm long segments using a diamond saw. For degradation studies, PPF/PPF-DA network films were obtained by polymerization of the PPF/PPF-DA mixture in a Teflon mold with 1 mm depth.

Mechanical Testing

The mechanical properties of the PPF/PPF-DA networks under compression were determined according to known methods. Specifically, ten formulations were designed to assess the effects of molecular weight of PPF-DA and double bond ratio of PPF/PPF-DA on the compressive strength at yield and compressive modulus. Compressive testing for strength and modulus was conducted on an 858 Material Testing System mechanical testing machine (MTS System Corp., Eden Prairie, Minn.) following the guidelines set in ASTM F451-95. Cylindrical samples 12 mm high and 6 mm in diameter were compressed at a crosshead speed of 1 mm/min until failure, with the stress versus strain curve recorded throughout. The compressive modulus was calculated as the slope of the initial linear portion of the stress-strain curve. The compressive strength at the yield was defined by drawing a line parallel to the slope defining the modulus, beginning at 1.0% strain. The intersection of this line with the stress-strain curve was recorded as the compressive strength at yield. The different formulations and their test results are set out in Table I.

TABLE 1

Formulation of ten PPF/PPF-DA (m = 1,3) networks. BP and DMT were 0.3 wt % and 0.15 wt %, respectively, for all formulations, based on the total amount of PPF and PPF-DA.

| Ex. No. | m | Weight ratio of PPF/PPF-DA | Double bond ratio of PPF/PPF-DA |
|---|---|---|---|
| 1 | 1 | 0 | 0 |
| 2 | 1 | 0.44 | 0.5 |
| 3 | 1 | 0.88 | 1 |
| 4 | 1 | 1.76 | 2 |
| 5 | 1 | 3.52 | 4 |
| 6 | 3 | 0 | 0 |
| 7 | 3 | 0.23 | 0.5 |
| 8 | 3 | 0.46 | 1 |
| 9 | 3 | 0.94 | 2 |
| 10 | 3 | 1.84 | 4 |

The PPF/PPF-DA double bond ratio and the molecular weight of PPF-DA were varied to asses their effects on the mechanical properties of the resulting polymer networks as well as on their equilibrium water content. The compressive strength at yield of PPF/PPF-DA (m=1) polymer networks increased from 11.7±1.1 to 91.0±10.2 MPa as the double bond ratio of PPF/PPF-DA (m=1) decreased from 4 to 0.5. An increase in compressive modulus was also observed from 66.4±9.4 to 568.2±82.1 MPa for the same range of the double bond ratio of PPF/PPF-DA. Increasing the molecular weight of PPF-DA (m=3) caused both the compressive strength at yield and modulus of the corresponding polymer networks to decrease to the ranges of 7.5±2.5 to MPa and 42.9±14.6 to 314.1±72.3 MPa respectively, while both were increased as the PPF/PPF-DA (m=3) double bond ratio decreased.

Figure 7:
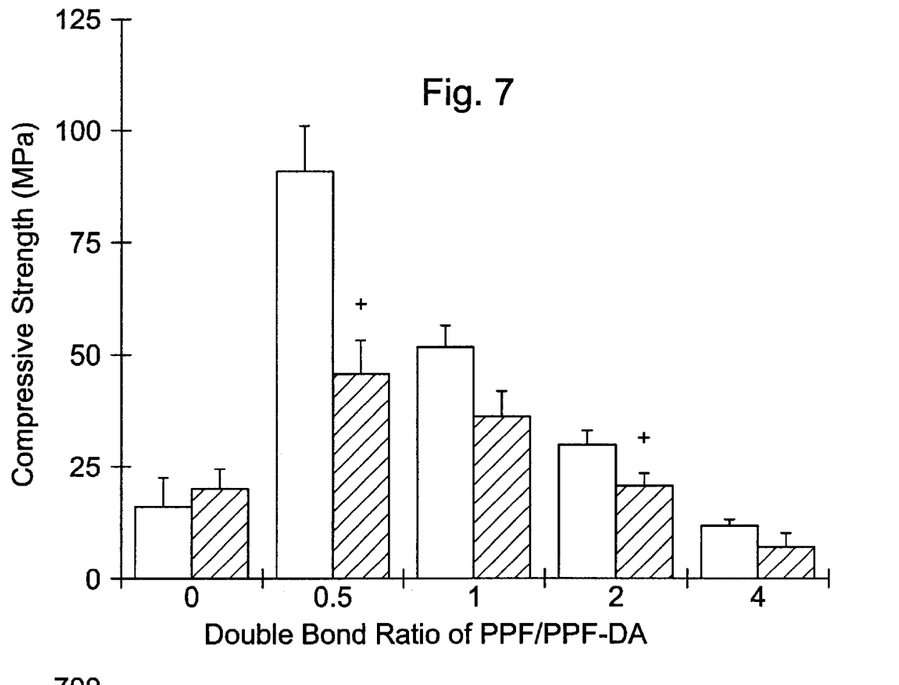
FIGS. 7 and 8 are plots showing the measured dependence of compressive strength at yield and compressive modulus at yield, respectively, of cross linked PPF/PPF-DA polymer networks on both the double bond ratio of PPF/PPF-DA and the molecular weight of PPF-DA (m=1, white bar; m=3, black bar)
Figure 8:
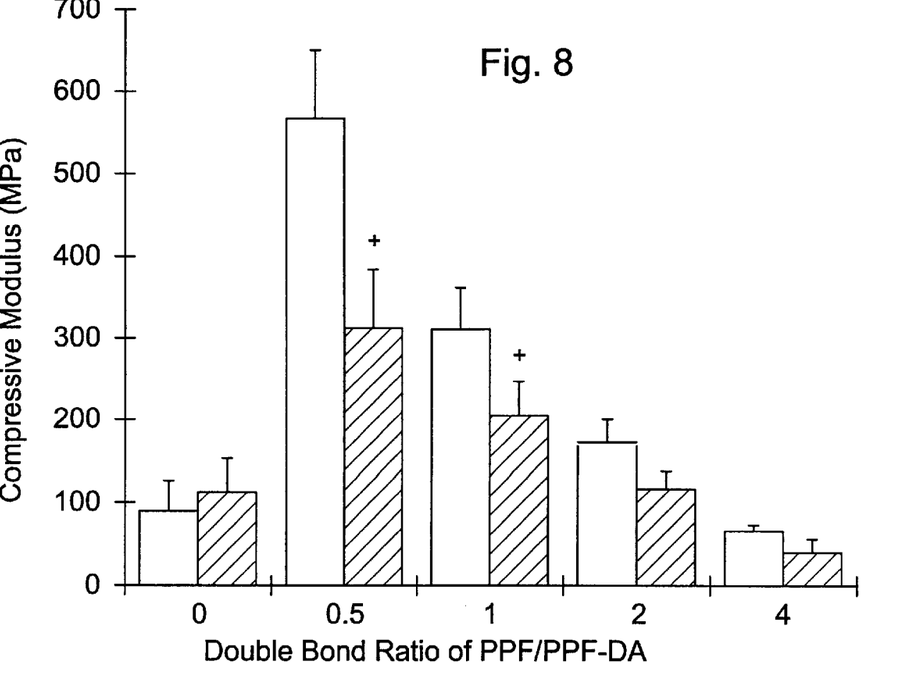

FIGS. 7 and 8 are plots showing the measured dependence of compressive strength at yield and compressive modulus at yield, respectively, of crosslinked PPF/PPF-DA polymer networks on both the double bond ratio of PPF/PPF-DA and the molecular weight of PPF-DA (m=1, white bar; m=3, black bar).

Water Content

The equilibrium water content of the present PPF/PPF-DA polymer networks was determined by gravimetry measurements, using cylindrical specimens of 6 mm diameter and 12 mm height prepared as outlined for the mechanical testing. The PPF/PPF-DA specimens were washed with methylene chloride, air-dried for one day, and vacuum-dried for 6 hours. The weight of the dried specimens was then recorded as $W_1$. The specimens were then immersed in phosphate buffered saline (PBS, pH 7.4) at room temperature. The weight of the specimens was monitored periodically and recorded when it reached an equilibrium value $W_2$, after approximately 24 hours. The equilibrium water content was calculated as $[(W_2-W_1)/W_2]\times 100$.

Figure 9:
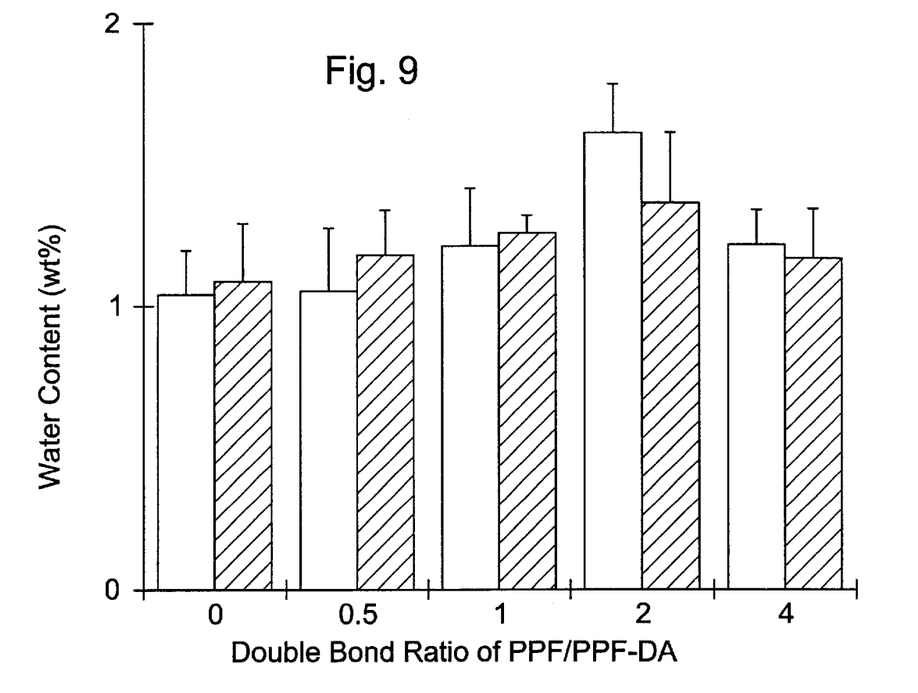
FIG. 9 is a plot showing equilibrium water content of cross linked PPF/PPF-DA polymer networks (m=1, white bar; m=3, black bar) as a function of the double bond ratio of PPF/PPF-DA.

Experiments for the equilibrium water content measurement were conducted in triplicate, while those for the mechanical testing were repeated five times. Single factor analysis of variance (ANOVA) was used to assess the statistical significance of the results. Scheffe's method was employed for multiple comparison tests at a significance level of 95% (p<0.05). FIG. 9 is a plot showing equilibrium water content of crosslinked PPF/PPF-DA polymer networks (m=1, white bar; m=3, black bar) as a function of the double bond ratio of PPF/PPF-DA. Error bars stand for means ± standard deviation.

Degradation Reaction of PPF/PPF-DA Networks

Because it is assumed that the biomaterials formed according to the present invention will degrade in an in vivo environment, samples of PPF/PPF-DA networks formed as described above were also subjected to degradation processes and analysis of the resulting products. Specifically, for degradation studies, PPF/PPF-DA network films were obtained by polymerization of the PPF/PPF-DA mixture in a Teflon mold having a depth of 1 mm.

Figure 10:
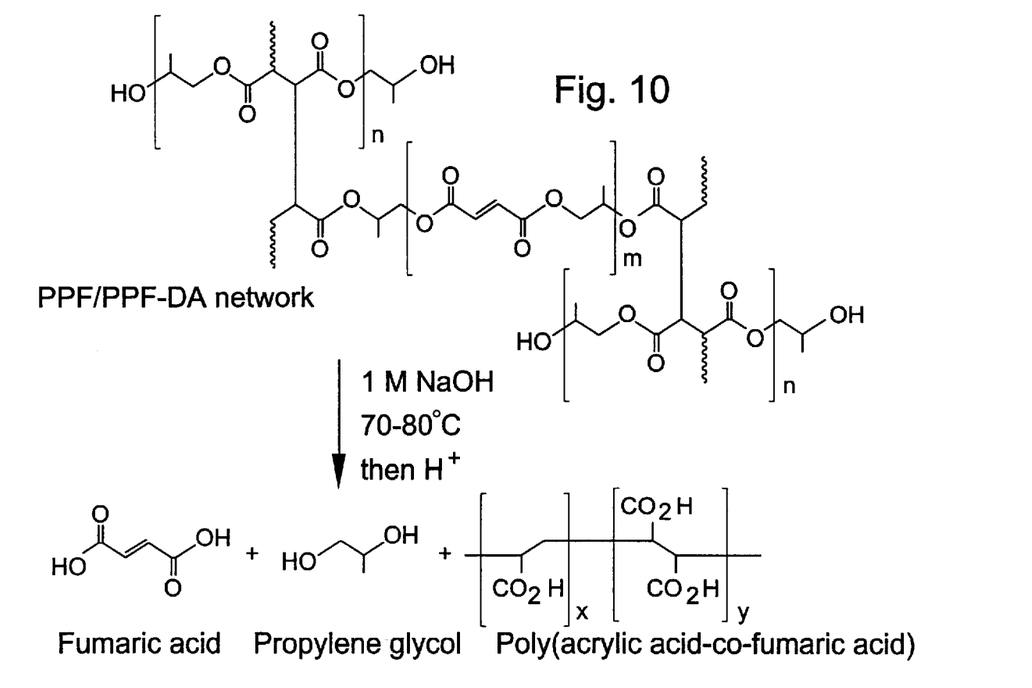
FIG. 10 is a schematic chemical diagram illustrating the degradation reaction of PPF/PPF-DA polymer networks.

An accelerated degradation reaction of PPF/PPF-DA networks was carried out under strongly basic conditions according to a mechanism such as that shown in FIG. 10, which is also believed to be the mechanism for biodegradation of the present compounds. 1.7 g PPF/PPF-DA networks were placed into 100 mL 1M NaOH solution and the reaction mixture was stirred at 70–80° C. under a nitrogen atmosphere until the polymer networks completely dissolved (approximately 4 days). The solution pH was adjusted to 1 by addition of 5% aq. HCl. The acidic solution was rotary evaporated to give a slushy residue. For NMR studies, the residue was extracted with acetone-$d_6$ (10 mL) for 20 min at room temperature. For GC and GC/MS, acetone was used to extract the degradation products. The undissolved residue was washed with acetone and dried under vacuum. To the slightly orange solid was added freshly prepared diazomethane in ether at room temperature until the yellow color of diazomethane persisted, suggesting completion of the reaction. As expected, gas evolution ($N_2$) was observed during this reaction. The ether was rotary evaporated and the product was extracted into $CHCl_3$ for GPC measurement.

The molecular weights of PPF and degradation copolymer were determined relative to polystyrene standards in chloroform by gel permeation chromatography with a conventional differential refractometer detector. A Styragel HR2 column (300×7.8 mm, 5 nm, mixed bed, Waters, Milford, Mass.) and a Phenogel guard column (50×7.8 mm, 5 nm, mixed bed, Phenomenex) were employed with a chloroform eluent flow rate of 1 mL/min.

Figure 12:
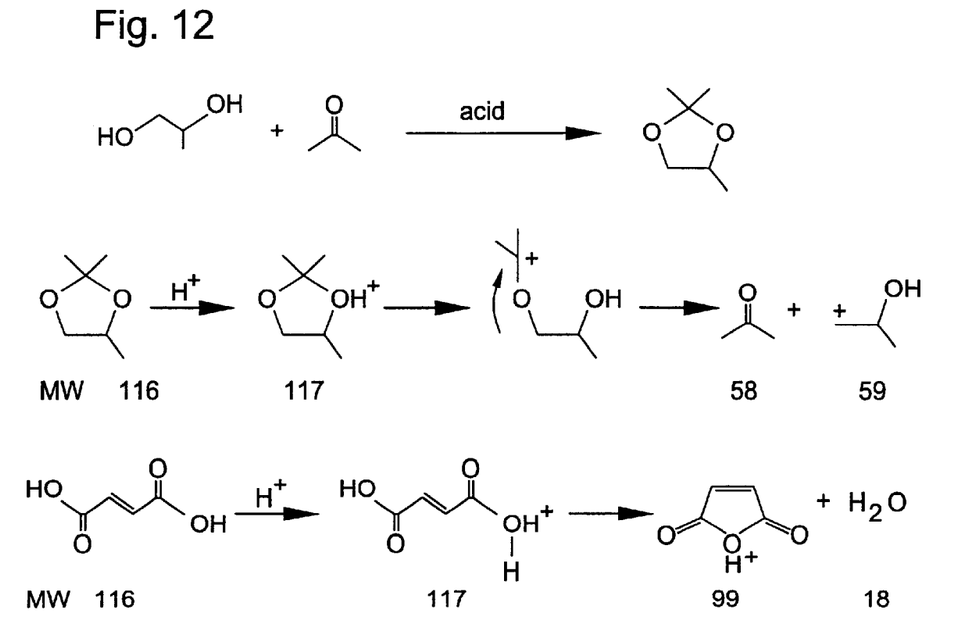
FIG. 12 shows MS/CI fragmentations of degradation products extracted by acetone.

For the GC analysis of the degradation products, acetone was chosen as a solvent to extract the monomeric products, because the possible degradation products, fumaric acid and propylene glycol, have relatively high solubility in acetone while poly(acrylic acid-co-fumaric acid) is barely soluble in it. Analytical gas chromatography (GC) was carried out on a HP 5890A instrument equipped with a AT1701 capillary column (0.25 mm×30 m) and FID detectors. Analytical GC conditions were 80° C. for 5 min, ramp at 10° C./min to 250° C., hold 10 min. GC/MS spectra were obtained on a Finnigan MAT 95 equipped with a DB-5 capillary column (0.25 mm×30 m). Both the singlet signal at 2.09 in (a) and the multiplets at 31.75 ppm in (b) belong to acetone-$d_6$. Two products having retention times of 4.7 and 15.7 min were detected. Based on GC/MS, both peaks have the same molecular weight of 116 and showed major fragments at m/e=59 and 99, respectively. Analysis of the MS pattern (FIG. 12) suggested that the two products were fumaric acid and propylene glycol acetonide.

Figure 11A:
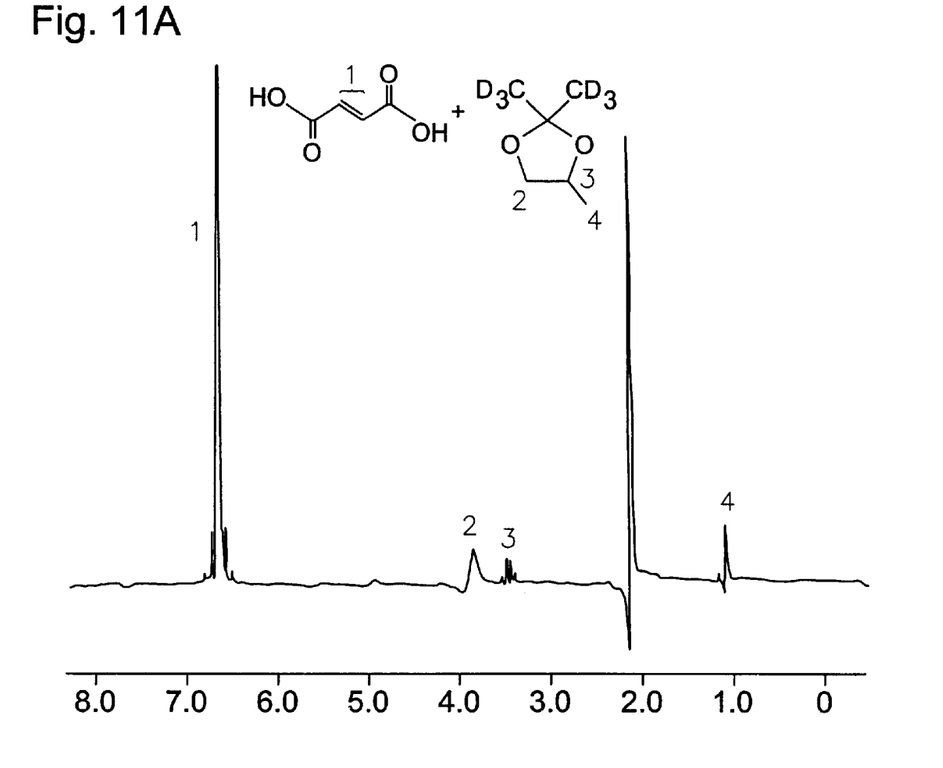
FIGS. 11A and 11B are $^1$H NMR and $^{13}$C NMR spectra, respectively, of the degradation products extracted into acetone-$d_6$.
Figure 11B:
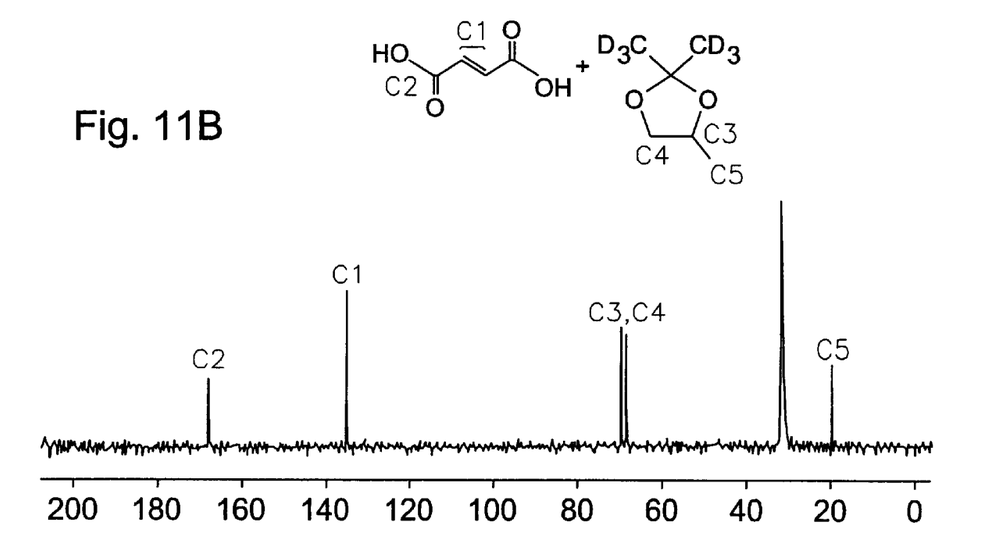

Support for these structural assignments resulted from NMR analysis of the degradation products extracted into deuterated acetone. As before, NMR and FTIR spectra were obtained for the product and both are shown in FIG. 11. In the $^1H$ NMR spectrum, four signals were found at 6.66, 3.82, 3.43, and 1.08 ppm. The large singlet peak at 6.66 ppm could belong to the two vinyl protons of fumaric acid, while the other three peaks arise from propylene glycol acetonide-$d^6$. The $^{13}C$ spectrum further confirmed these assignments. The carbonyl group was found at 167.6 ppm, while the chemically equivalent vinyl carbons were at 134.7 ppm. The methyl carbon in propylene glycol acetonide was assigned to the peak at 19.0 ppm, while the other two carbons should be at the peaks at 67.5 and 68.9 ppm.

Propylene glycol acetonide came from the reaction of propylene glycol and acetone under acid catalysis. During the work-up of the degradation reaction, strong acid, HCl, was used to convert the degraded sodium salts to the corresponding acids in order to render them soluble in organic solvents. When acetone was used as the extracting solvent, the propylene glycol was converted completely to its acetonide under the acidic conditions.

Fumaric acid resulted from the uncrosslinked fumarate unit in both PPF and PPF-DA. This result indicates that only a fraction of the fumarate double bonds in PPF participated in the crosslinking reaction to form PPF polymer networks. The absence of acrylic acid in the degradation product mixture indicated that all acrylate groups in PPF-DA were consumed in the crosslinking reaction, even though the double bond ratio of PPF/PPF-DA exceeded 1. This result implies that self-polymerization of PPF-DA was also involved in the crosslinking reaction.

The acetone-insoluble degradation product, poly(acrylic acid-co-fumaric acid), did not dissolve in other organic solvents including $CHCl_3$. In order to determine the molecular weight of this copolymer, it was converted to the corresponding methyl ester. After treatment with diazomethane, the esterified copolymer was soluble in $CHCl_3$ for GPC measurement. The GPC result showed that this material had a number average molecular weight of 2,340 and a weight average molecular weight of 5,080. These molecular weights are well below the threshold value of 70,000 for hydrophilic polymers that are passively excreted by the kidneys.

Results and Discussion

Synthesis of PPF and PPF-DA

As discussed previously, it is known that the molecular weight of PPF can be controlled by varying the transesterification time. The $^1H$ NMR spectrum of PPF (FIG. 2) shows four multiplets. The signal at 6.84 ppm is assigned to the olefinic protons, while the 1.27 ppm peak is attributed to the methyl protons. The other two signals, at 5.28 and 4.28 ppm, belong respectively to the methine and methylene protons of the propyl diol. The integration ratio of the vinyl protons to the methyl protons is 2/3.6, which is close to the 2/3.4 calculated based on the number average molecular weight of PPF. This agreement indicated no loss of polymer unsaturation during the two step synthesis.

PPF-DAs with m=1 and m=3 were synthesized by reaction of the appropriate PPF with acryloyl chloride. It was found from the $^1H$ NMR spectrum (FIG. 5) of PPF-DA (m=1) that integration ratio of acryl protons to fumarate protons is 3 to 1. This ratio suggested that both terminal hydroxyl groups in di-(2-hydroxylpropyl) fumarate are derivatized with an acrylate group. Further evidence of reaction at both ends came from the FTIR spectrum of PPF-DA (FIG. 3), which showed no OH stretching band in the region of 3500–3100 cm-1. The PPF with m=3 was produced in the same way using PPF with m=3 obtained after 4 hours of transesterification. The integration ratio of acrylate to fumarate vinyl protons allows determination of the molecular weight of PPF-DA. The $^1H$ NMR spectrum gives the ratio of 1:1, which implies presence of 3 fumarate units in this PPF-DA. Mechanical properties As shown in FIGS. 8 and 9, the compressive strength of PPF/PPF-DA (m=1) ranged from 11.7±1.1 to 91.0±10.2 MPa and the modulus was in the range of 66.4±9.4 to 568.2±82.1 MPa. In FIGS. 8 and 9, error bars stand for means ± standard deviation for n=5. A symbol "+" represents the statistically significant difference of pairwise comparison for crosslinked PPF/PPF-DA networks with different molecular weight of PPF-DA. Each increased as the double bond ratio of PPF/PPF-DA decreased (p<0.05). The decrease of the PPF/PPF-DA double bond ratio increases the fraction of the more reactive acrylate group, which increases the efficiency of crosslinking, creating a more densely crosslinked polymeric network. When the double bond ratio of PPF/PPF-DA is zero (absence of PPF), the compressive strength and modulus drop to 15.6±6.5 MPa and 85.9±42.3 MPa, respectively. The self-polymerization of PPF-DA rather than crosslinking to PPF may dominate and generate long crosslinks, decreasing the mechanical properties, when the PPF/PPF-DA double bond ratio is too low.

When the propylene fumarate chain linking two acrylate groups in PPF-DA was lengthened, the crosslinks of the PPF/PPF-DA polymeric networks also extended, leading to the decrease of mechanical properties. The compressive strength at yield and modulus of the PPF/PPF-DA (m=3) decreased to the ranges of 7.5±2.5 to 45.5±7.5 MPa and 42.9±14.6 to 314.1±72.3 MPa, respectively, in the same range of PPF/PPF-DA (m=3) double bond ratio, while both were still increased as the PPF/PPF-DA double bond ratio decreased ($p<0.05$).

These results demonstrate that the mechanical properties of PPF/PPF-DA polymeric networks can be tailored by varying not only the PPF/PPF-DA double bond ratio, but also the length of the PPF-DA. Formation of polymer networks from PPF-DA alone indicated that the fumarate groups in PPF-DA might also be involved in the crosslinking reaction. It was also found that the mechanical properties of the polymer networks produced from PPF-DA alone did not increase significantly as the molecular weight of PPF-DA increased from 340 to 650. In comparison with other crosslinked PPF composites, the PPF/PPF-DA polymeric networks tested in this study showed a wide range of compressive strength at yield and compressive modulus upon varying the double bond ratio of PPF/PPF-DA or the length of PPF-DA. This suggests that it is possible to formulate biodegradable PPF-based compositions having a wider range of mechanical properties than has previously been possible.

Similarly, the water absorption data give promising results. Unlike PPF/PEG-DMA networks, PPF/PPF-DA networks show very low water absorption, probably due to the hydrophobic properties of both PPF and PPF-DA. The low water absorption capacity may protect the networks against diminution of their mechanical properties in the wet state.

CONCLUSIONS

New biodegradable poly(propylene fumarate)-based polymer networks can be synthesized by radical reaction of PPF and newly synthesized PPF-DA. These networks can alternatively be referred to as "gels." The present PPF/PPF-DA polymer networks possess strong mechanical properties. The compressive strength and modulus of the PPF/PPF-DA polymer networks tested spanned a wide range and were mainly affected by the PPF/PPF-DA double bond ratio and the molecular weight of PPF-DA. All crosslinked networks showed very low water absorption. These polymer networks degrade by hydrolysis of the ester linkage to biocompatible, water-soluble products that include propylene glycol, fumaric acid, and poly(acrylic acid-co-fumaric acid). The good mechanical properties and degradation to biocompatible products make these new PPF/PPF-DA polymer networks well-suited for use as biomaterial scaffolds in orthopaedic tissue engineering.

What is claimed is:

1. A poly(propylene fumarate) cross linked with poly(propylene fumarate)-diacrylate.

2. A cross linkable composition comprising poly(propylene fumarate)-diacrylate and poly(propylene fumarate).

3. A polymeric network comprising poly(propylene fumarate) cross linked with poly(propylene fumarate)-diacrylate.

4. The composition according to claim 3 having a compressive strength at yield of at least 11.7 MPa.

5. The composition according to claim 3 having a compressive modulus of at least 66.4 MPa.

6. The composition according to claim 3 wherein said composition degrades to a hydrophilic polymer capable of being passively excreted by human kidneys.

7. The composition according to claim 3 wherein the cross linked poly(propylene fumarate)-diacrylate has an equilibrium water content less than 1.5 percent by weight.

8. A composition suitable for use as a biocompatible implant, comprising:

a poly(propylene fumarate) network crosslinked with poly(propylene fumarate)-diacrylate macromers.

9. The composition according to claim 8 having a compressive strength at yield of at least 11.7 MPa.

10. The composition according to claim 8 having a compressive modulus of at least 66.4 MPa.

11. The composition according to claim 8 wherein said composition degrades to a hydrophilic polymer capable of being passively excreted by human kidneys.

12. A poly(propylene fumarate) network crosslinked with poly(propylene fumarate)-diacrylate and suitable for use as a biocompatible implant, having the formula:

* * * * *